(12) United States Patent
Kehres et al.

(10) Patent No.: US 9,700,438 B2
(45) Date of Patent: Jul. 11, 2017

(54) ORTHOPAEDIC INSTRUMENT FOR SECURING A BONE

(71) Applicant: Biomet Manufacturing, LLC, Warsaw, IN (US)

(72) Inventors: Clinton Kehres, Warsaw, IN (US); Nicholas Muir, Winona Lake, IN (US); Andrew O'Reilly, Jefferson, OH (US); John McDaniel, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 542 days.

(21) Appl. No.: 14/297,559

(22) Filed: Jun. 5, 2014

(65) Prior Publication Data

US 2015/0297361 A1    Oct. 22, 2015

Related U.S. Application Data

(60) Provisional application No. 61/981,245, filed on Apr. 18, 2014.

(51) Int. Cl.
| | |
|---|---|
| A61F 2/46 | (2006.01) |
| A61B 17/15 | (2006.01) |
| B25B 5/10 | (2006.01) |
| B25B 5/14 | (2006.01) |
| B25B 5/16 | (2006.01) |
| A61B 17/88 | (2006.01) |
| A61F 2/30 | (2006.01) |

(52) U.S. Cl.
CPC ............ *A61F 2/4644* (2013.01); *A61B 17/15* (2013.01); *B25B 5/102* (2013.01); *B25B 5/147* (2013.01); *B25B 5/163* (2013.01); *A61B 17/8866* (2013.01); *A61F 2002/3096* (2013.01); *A61F 2240/002* (2013.01)

(58) Field of Classification Search
CPC  A61F 2/4644; A61B 2017/2808; A61B 17/15
See application file for complete search history.

(56) References Cited

U.S. PATENT DOCUMENTS

| | | | | |
|---|---|---|---|---|
| 5,021,056 | A  * | 6/1991 | Hofmann | A61B 17/15 606/86 R |
| 5,667,512 | A  * | 9/1997 | Johnson | A61B 17/158 606/87 |
| 6,648,894 | B2 * | 11/2003 | Abdelgany | A61F 2/4644 606/53 |
| 6,676,662 | B1 * | 1/2004 | Bagga | A61B 17/15 606/87 |
| 7,722,608 | B2 * | 5/2010 | Steiner | A61F 2/4644 269/54.1 |
| 7,780,668 | B2 * | 8/2010 | Steiner | A61F 2/4644 269/87 |

(Continued)

*Primary Examiner* — Andrew Yang
(74) *Attorney, Agent, or Firm* — Schwegman Lundberg & Woessner, P.A.

(57) ABSTRACT

An orthopedic instrument for securing a bone includes a base plate, a cutting block removably coupled with an end of said base plate, and a V-shaped vice member slidingly coupled with the base plate and movable toward and away from the cutting block. The cutting block has a plurality of cutting slots, each of which has a predefined configuration. Further, the vice member is configured for centering the bone and applying a force against the bone toward the cutting block.

20 Claims, 13 Drawing Sheets (56) References Cited

U.S. PATENT DOCUMENTS

| | | | |
|---|---|---|---|
| 8,127,646 B2* | 3/2012 | Couvillion | A61B 17/1635 83/34 |
| 8,800,158 B1* | 8/2014 | Shim | A61B 17/1635 33/630 |
| 2004/0034361 A1* | 2/2004 | Dalton | A61B 17/15 606/87 |
| 2004/0097946 A1* | 5/2004 | Dietzel | A61B 17/15 606/79 |

* cited by examiner

ORTHOPAEDIC INSTRUMENT FOR SECURING A BONE

CROSS REFERENCE TO RELATED APPLICATIONS

This is a non-provisional application based upon U.S. provisional patent application Ser. No. 61/981,245, entitled "ORTHOPAEDIC INSTRUMENT FOR SECURING A BONE", filed Apr. 18, 2014, which is incorporated herein by reference.

BACKGROUND OF THE INVENTION

1. Field of the Invention

The present invention relates to an orthopaedic instrument, and, more particularly, to an orthopaedic instrument for securing and shaping a bone.

2. Description of the Related Art

Orthopaedic patients needing total joint replacement surgery are often found to have severe, pathologic bone loss at the affected joint. In this type of scenario, surgeons often use various types of bone shaping and bone grafting techniques to replace the worn bone. Surgeons are often tasked with having to create a custom-shaped bone manually with only visual guidance. This is not only time consuming, but also very difficult.

What is needed in the art is an orthopaedic instrument which fixedly secures the bone in place so that a surgeon can efficiently produce a custom-shaped bone with a high degree of accuracy.

SUMMARY OF THE INVENTION

The present invention provides an orthopaedic instrument having a V-shaped vice member for centering and securing a bone in position for custom shaping of the bone for a patient according to a number of predetermined parameters. A bone in the context of the present application includes both natural and synthetic bone material, and further includes excised bone and bone grafts.

The invention in one form is directed to an orthopaedic instrument for securing a bone, which includes base plate, a cutting block removably coupled with an end of the base plate, and a V-shaped vice member slidingly coupled with the base plate toward and away from the cutting block. The cutting block has a plurality of cutting slots, each of which has a predefined configuration. Further, the V-shaped vice member is configured for centering the bone and applying a force against the bone toward the cutting block.

The invention in another form is directed to an orthopaedic instrument for securing a bone, including a base plate, a cutting block removably coupled with an end of the base plate, and a V-shaped vice member slidingly coupled toward and away from the cutting block with the base plate. The cutting block includes a plurality of cutting slots having a predefined orientation and is configured for applying a force against the bone toward the base plate. Further, the V-shaped vice member is configured for applying another force to the bone toward the base plate and for applying a third force to the bone toward the cutting block.

The invention in yet another form is directed to a method of producing a custom bone, which includes removably locking a cutting block to an end of a base plate and slidably coupling a V-shaped vice member with the base plate. The bone is inserted between the V-shaped vice member and the base plate. The V-shaped vice member is slidingly adjusted to a position against the bone and a force is applied with the V-shaped vice member against the bone toward the cutting block. The vice member is locked into the position against the bone to secure the bone in position against the cutting block. The bone is then custom-shaped.

An advantage of the present invention is that the orthopaedic instrument of the present invention effectively secures a bone in position, leaving each of the surgeon's hands free to shape the bone to customize it for a patient's specific needs. This avoids the risk of dropping the bone or the bone slipping during the shaping process, resulting in a damaged or unusable bone.

Another advantage is that the bone is secured during the shaping and sizing process increasing the successful customization of the bone to fit the patient's specific needs.

Yet another advantage is the orthopaedic instrument of the present invention is modularity for ease of cleaning.

Additionally, the uniquely shaped vice member centers the bone and at the same time forces the graft into the base plate and against the cutting block.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Referring now to the drawings, and more particularly to FIGS. 1A, 1B, 2 and 3, there is shown an orthopaedic instrument 10 which generally includes a base plate 12, a cutting block 14 and a V-shaped vice member 16.

Figure 2:
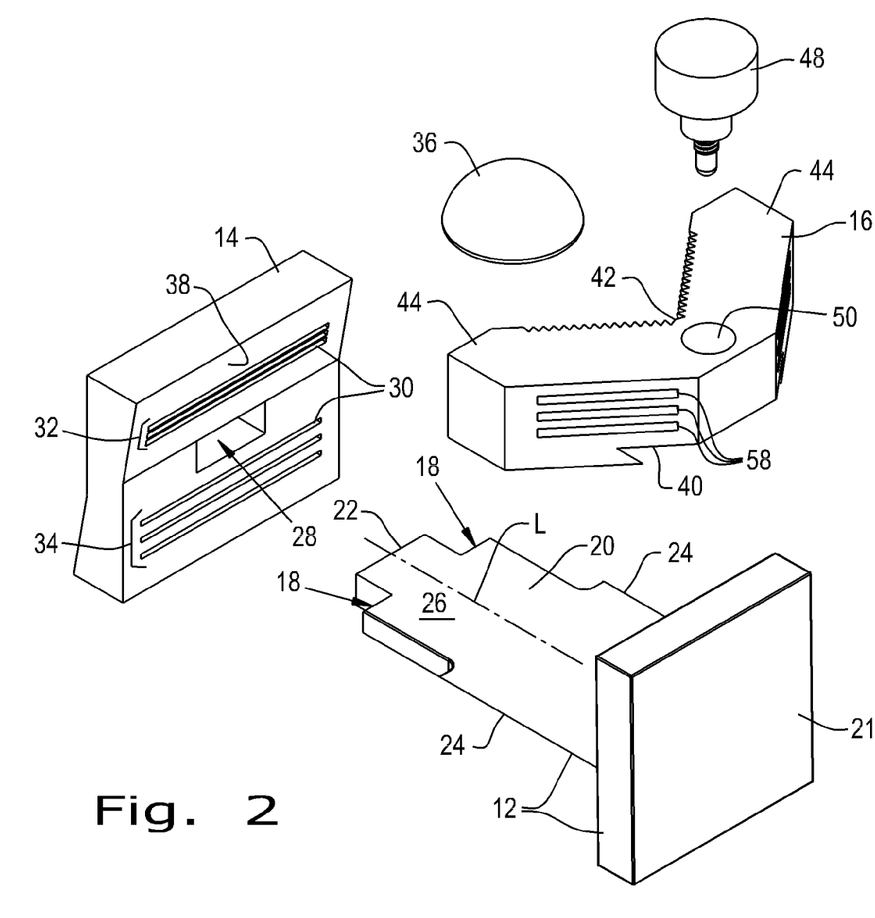
FIG. 2 is an exploded perspective view of the orthopaedic instrument of FIGS. 1A and 1B.
Figure 3:
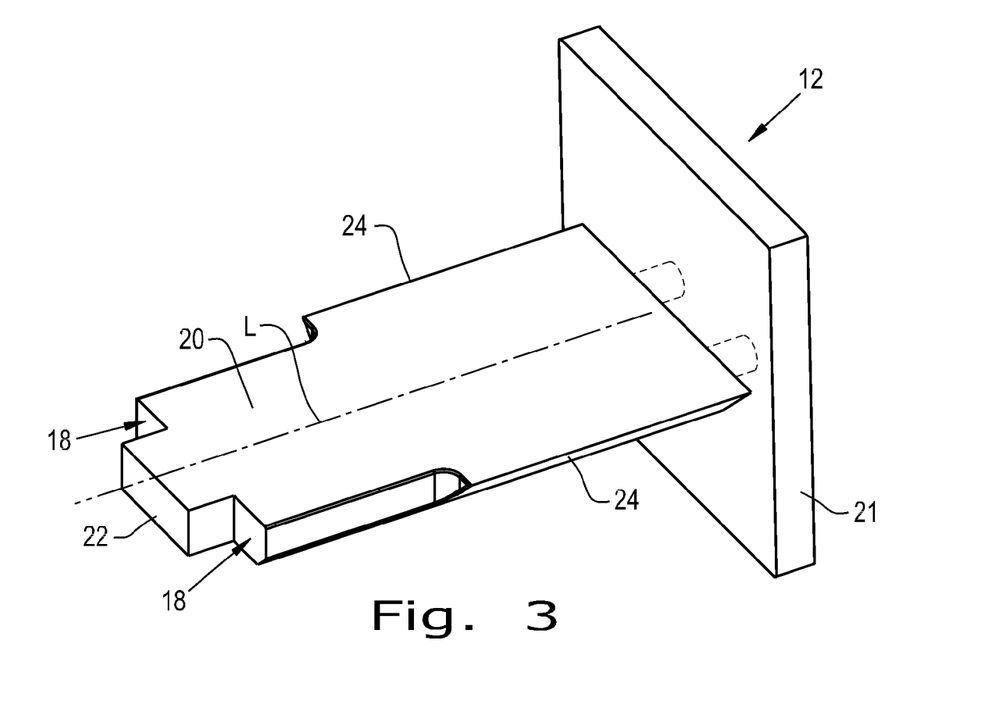
FIG. 3 is a perspective view of the base plate shown in FIGS. 1A, 1B and 2.
Figure 4:
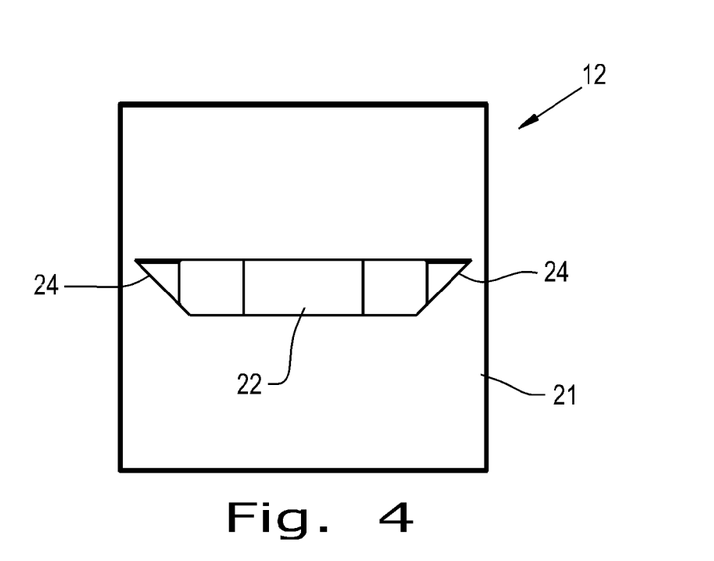
FIG. 4 is a sectional end view of the base plate illustrated in FIGS. 1A-3.

Base plate 12 is configured at one end 18 to be coupled with cutting block 14 (FIG. 2). Base plate 12 can be formed as a single, integral unit, or be formed from multiple pieces, removably coupled together for ease of cleaning after use. Base plate 12 includes an elongate planar portion 20 which extends along a longitudinal axis L of base plate 12 and a second portion 21, coupled with and transverse to elongate planar portion 20. Base plate 12 can further include a protrusion 22, for example in the form of a tongue for a tongue and groove joint, extending from end 18 of elongate planar portion 20, as is shown in FIGS. 2 and 3. Base plate 12 includes an elongate member 24 for coupling base plate 12 with vice member 16, for example a tenon 24, such as a dovetail-shaped tenon, defining a surface 26 of elongate planar portion 20, as illustrated in FIG. 4. It is, however, also feasible for elongate member 24 to be in the form of a groove (not shown) in surface 26 of elongate planar portion 20 of base plate 12 for slidingly receiving vice member 16.

Referring now to FIGS. 1A, 1B, 2, and 5-7, cutting block 14 in one embodiment of the present invention is configured as a single component piece having a through-opening 28, which is sized and shaped to securely receive protrusion 22 of base plate 12, thereby removably coupling cutting block 14 with base plate 12. Further, cutting block 14 may be secured to base plate 12 using a snap fit, one or more screws, or bolts, or any other fastener configured for removably coupling the components.

Figure 5:
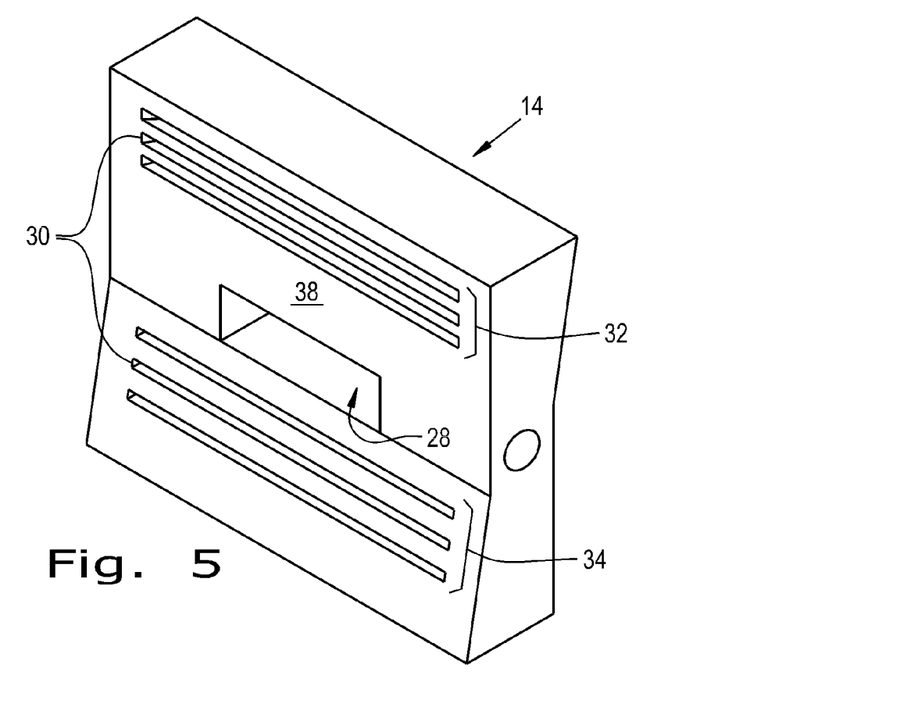
FIG. 5 is a perspective view of the cutting block shown in FIGS. 1A-2.
Figure 6:
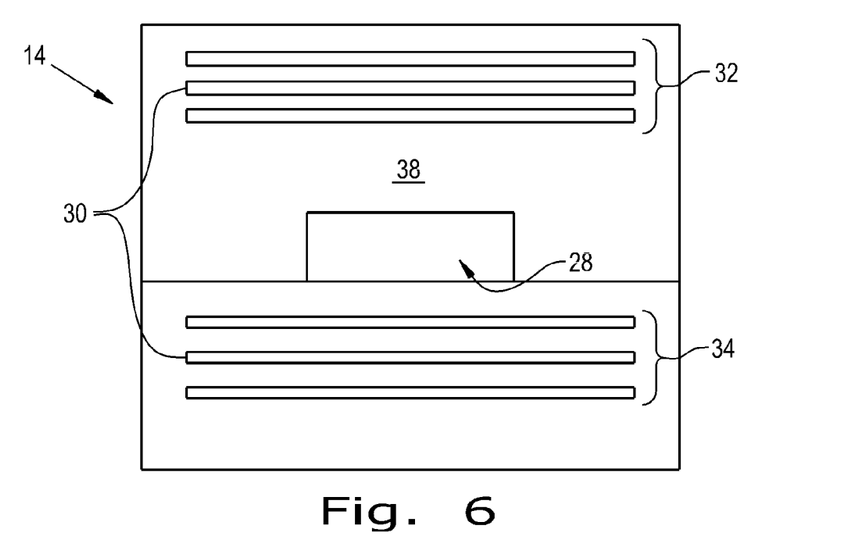
FIG. 6 is a side view of the cutting block of FIGS. 1A-2 and 5.
Figure 7:
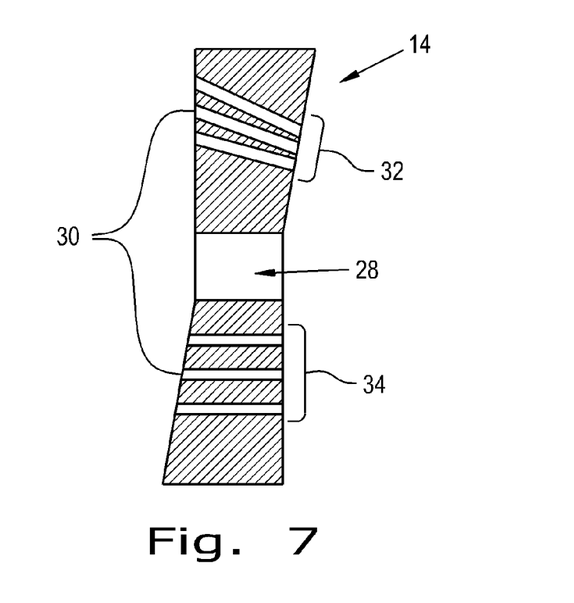
FIG. 7 is a sectional end view of the cutting block of FIGS. 1A-2 and 5-6.

Cutting block 14 includes a plurality of cutting slots 30, arranged in a predefined pattern and each of cutting slots 30 having a predefined configuration. For example, cutting slots 30 can be arranged such that a first set 32 of cutting slots are non-coplanar with elongate planar portion 20 base plate 12 and a second set 34 of cutting slots 30, which are substantially coplanar with base plate 12. The second set 34 of cutting slots 30, for example, can be positioned at a predefined distance, for example 5 millimeters (mm), 10 mm, and/or 15 mm, from base plate 12 when assembled. Although the predefined distance is set forth above, ranging from 5 to 15 millimeters from the base plate 12, second set 32 of cutting slots can be at any reasonable distance from base plate 12 which would be useful for cutting a bone 36 positioned within the orthopaedic instrument 10 according to the present invention.

Cutting block 14 is further, for example, configured for applying force against bone 36 toward elongate planar portion 20 of base plate 12. For example, cutting block 14 has a face 38 that increasingly extends toward V-shaped vice member 16 as it extends away from a plane of elongate planar portion 20 of base plate 12 when orthopaedic instrument 10 is assembled. Cutting block 14 is further configured to be rotatable 180 degrees to switch from first set 32 of cutting slots 30 to second set 34 of cutting slots 30 and vice versa.

Figure 1A:
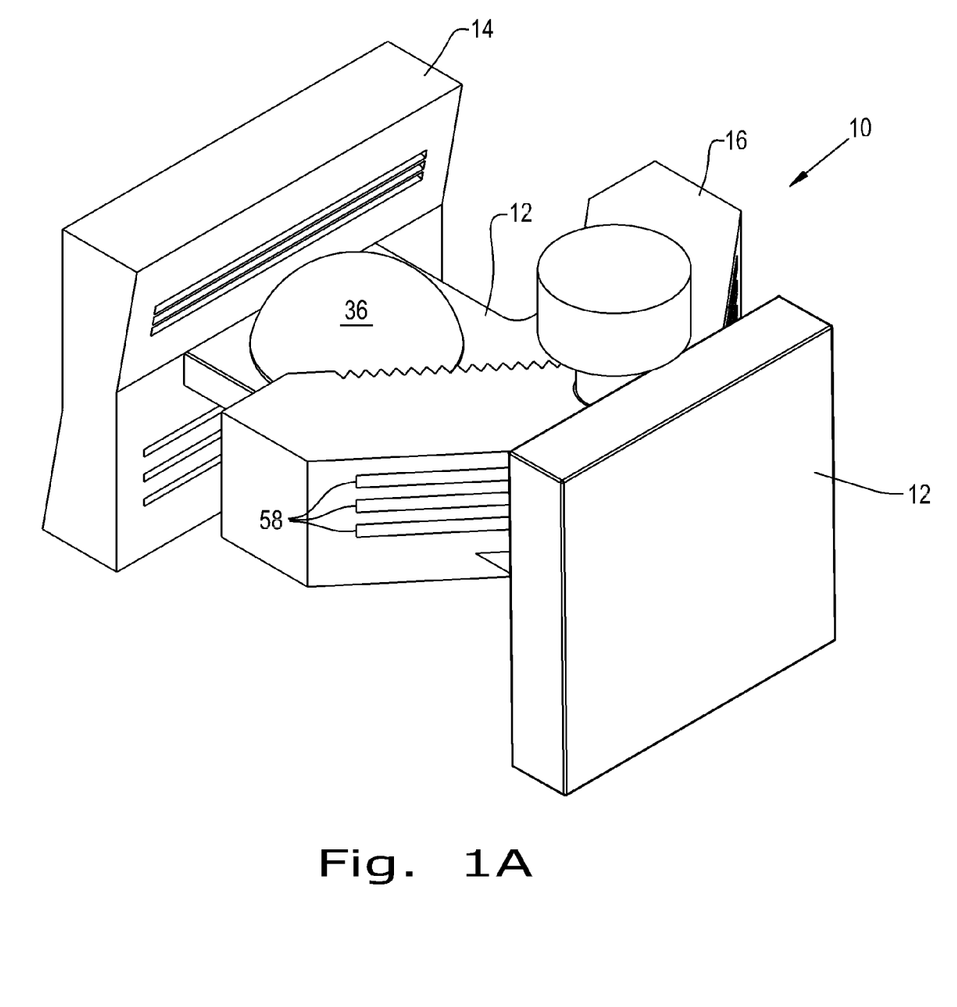
FIG. 1A is a perspective view of an embodiment of an orthopaedic instrument according to the present invention in a horizontal position.
Figure 1B:
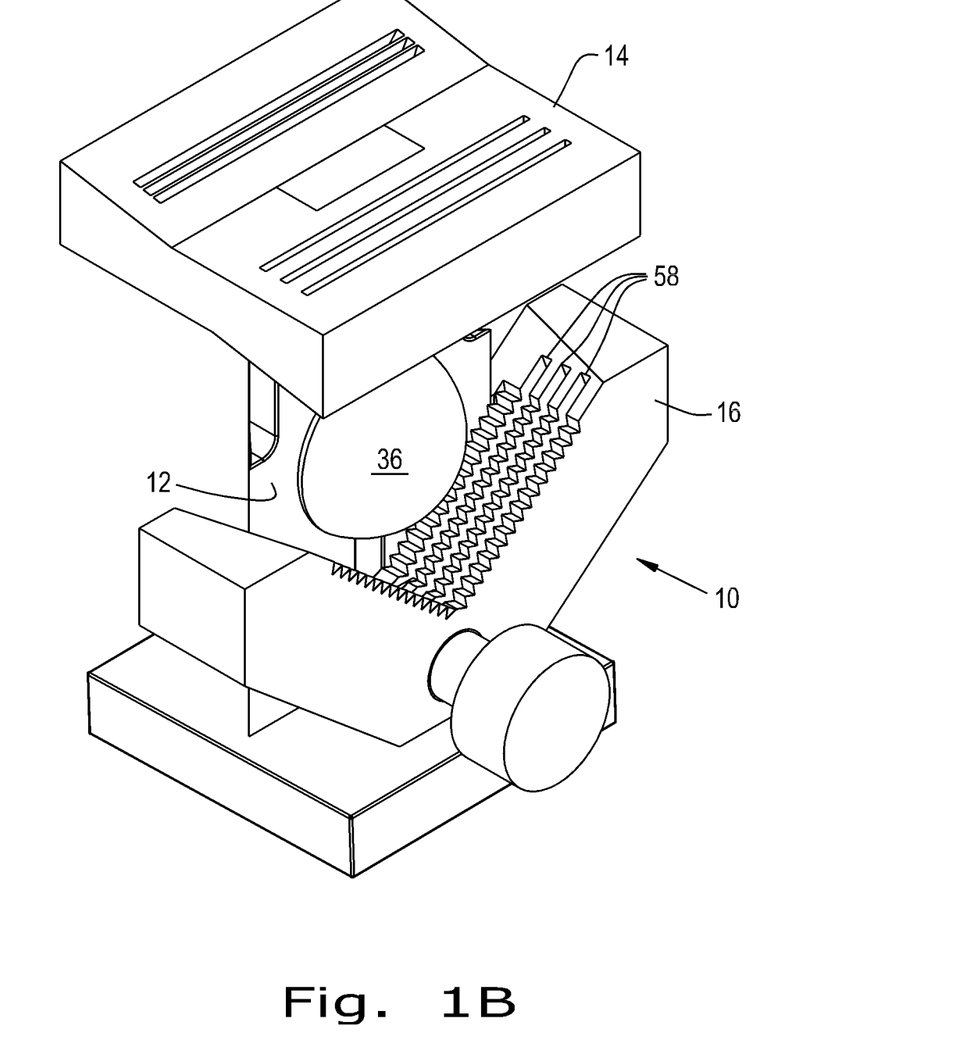
FIG. 1B is a perspective view of the orthopaedic instrument of FIG. 1A in a vertical position.

Referring now to FIGS. 1A, 1B, 2, and 8-9, there is shown V-shaped vice-member 16 which is slidingly coupled with base plate 12 toward and away from cutting block 14. (FIGS. 1A and 1B). V-shaped vice member 16 includes a coupling member 40 (FIG. 2) which is sized and shaped to be slidingly coupled with elongate member 24 of base plate 12. For example, V-shaped vice member 16 can include a dovetail-shaped mortise 40 (FIGS. 2 and 8) for receiving a corresponding dovetail-shaped tenon 24 of base plate 12 (FIGS. 2-4), or vice versa. Alternatively, vice member 16 can include a thumb screw (not shown) or other protrusion which is sized and shaped to be slidingly received within a groove (not shown) of base plate 12.

According to the present invention, V-shaped vice member 16 is configured for centering bone 36 and applying a force against bone 36 toward cutting block 14, as shown in FIGS. 1A and 1B. Referring now to FIG. 2, V-shaped vice member 16 centers bone 36 at an apex 42 of a pair of arms 44 forming the V-shape of vice member 16, thereby securing bone 36 against an inside surface of vice member 16. Vice-member 16 is then slidingly positioned in a lateral direction toward cutting block 14 to firmly secure bone 36 between cutting block 14 and vice member 16. A fastener 48 is inserted into a receiving aperture 50 of vice member 16 to secure vice member 16 in place relative to bone 36 and base member 12. Fastener 48 can be in the form of a thumb screw, a bolt, a pin, a clip or a screw, such as a set screw, or any other fastener known in the art.

Figure 8:
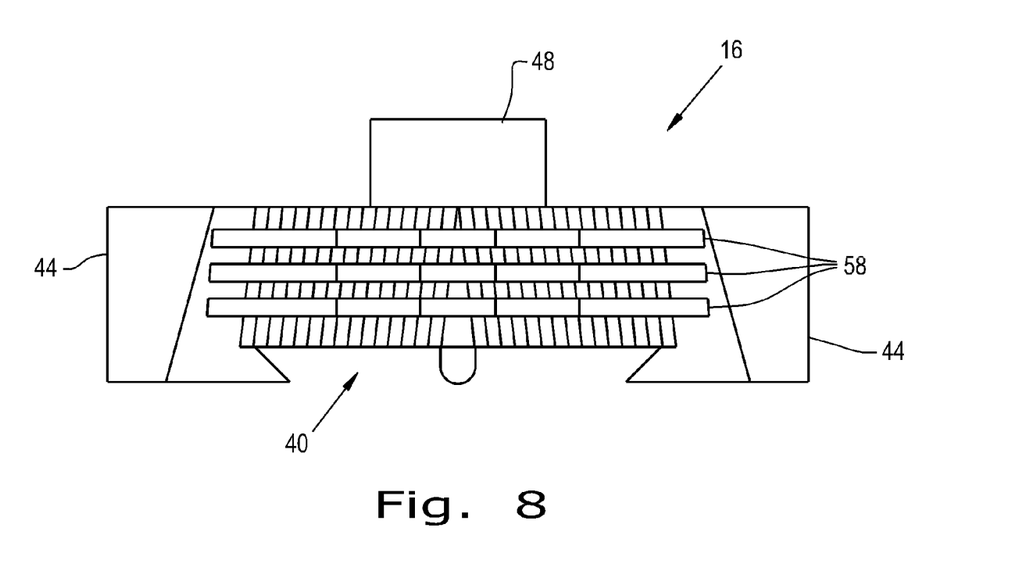
FIG. 8 is an end view of the vice member shown in FIGS. 1A-2.
Figure 9:
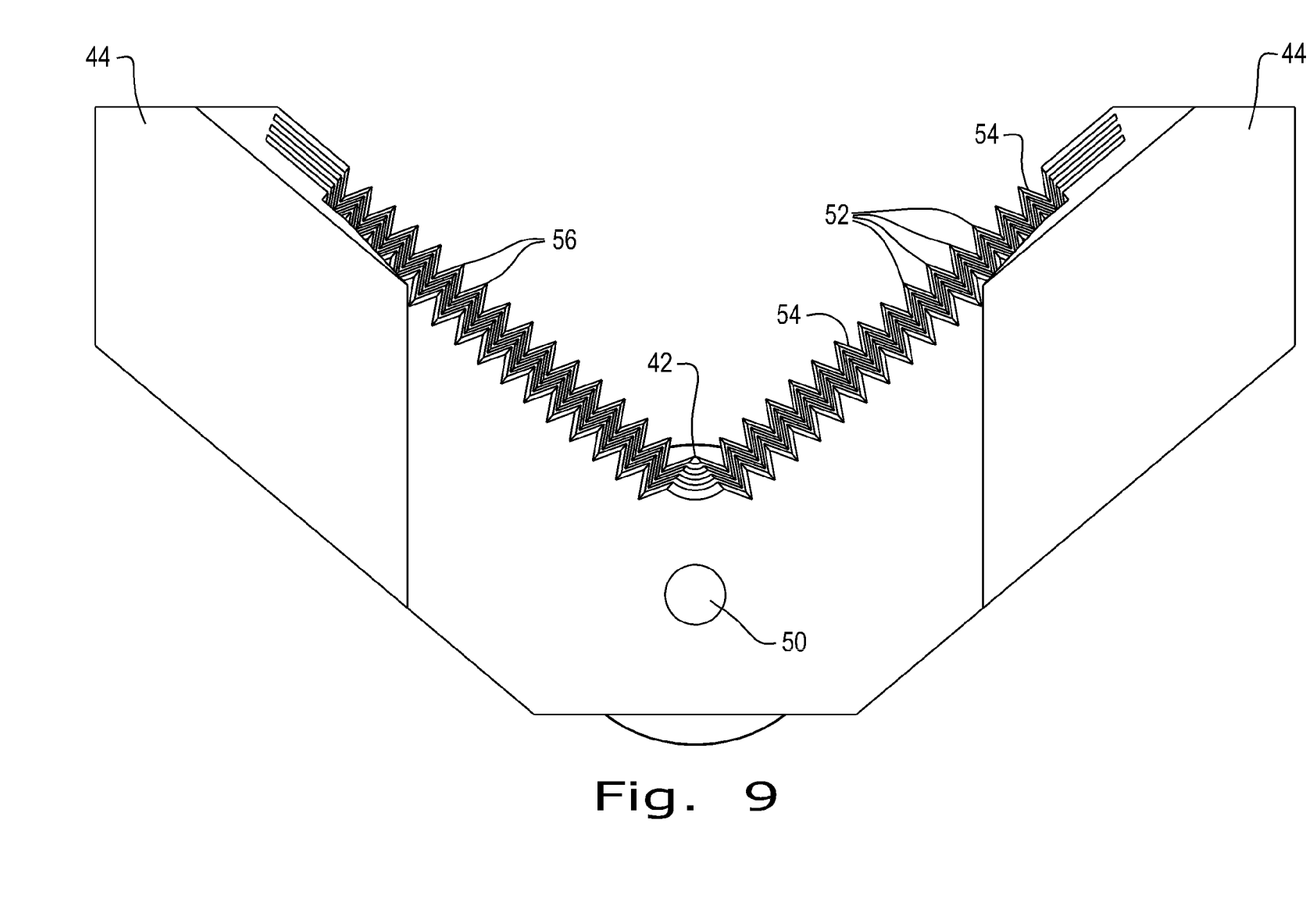
FIG. 9 is a bottom view of the vice member of FIGS. 1A-2 and 8.

Vice-member 16 can further be configured for applying a force against bone 36 toward base plate 12. For example, vice member 16 can include a plurality of teeth 52 extending from an inside surface of arms 44. Additionally, teeth 52 can be angled toward elongate planar portion 20 of base plate 12 when orthopaedic instrument 10 is assembled. Teeth 52 can, for example, be arranged in layers 54, for example 2, 3, 4 or more layers 54, and can further be positioned such that a pointed end 56 of a layer 54 of teeth 52 distal from elongate planar portion 20 of cutting block 14 when orthopaedic instrument 10 is assembled extends beyond next layer 54 of teeth 52 proximal to elongate planar portion 20 of base plate 12, and so on and so forth, such that teeth 52 of vice member 16 apply pressure against bone 36 toward elongate planar portion 20 of base plate 12.

Vice member 16 can include a plurality of supplemental cutting slots 58 (FIGS. 1A, 1B, and 2) extending through the arms 44 thereof for additional flexibility using a reciprocating saw blade for shaping bone 36.

The assembled orthopaedic instrument 10 is configured for use in a first orientation, as illustrated in FIG. 1A for a horizontal cutting plane, or a second orientation, whereby orthopaedic instrument 10 rests on second portion 21 of base plate 20, with elongate planar portion 20 extending vertically, for a vertical cutting plane, illustrated in FIG. 1B. It is also possible to mount orthopaedic instrument 10 on a rotational mount (not shown) for infinite possible cutting planes.

Figure 10:
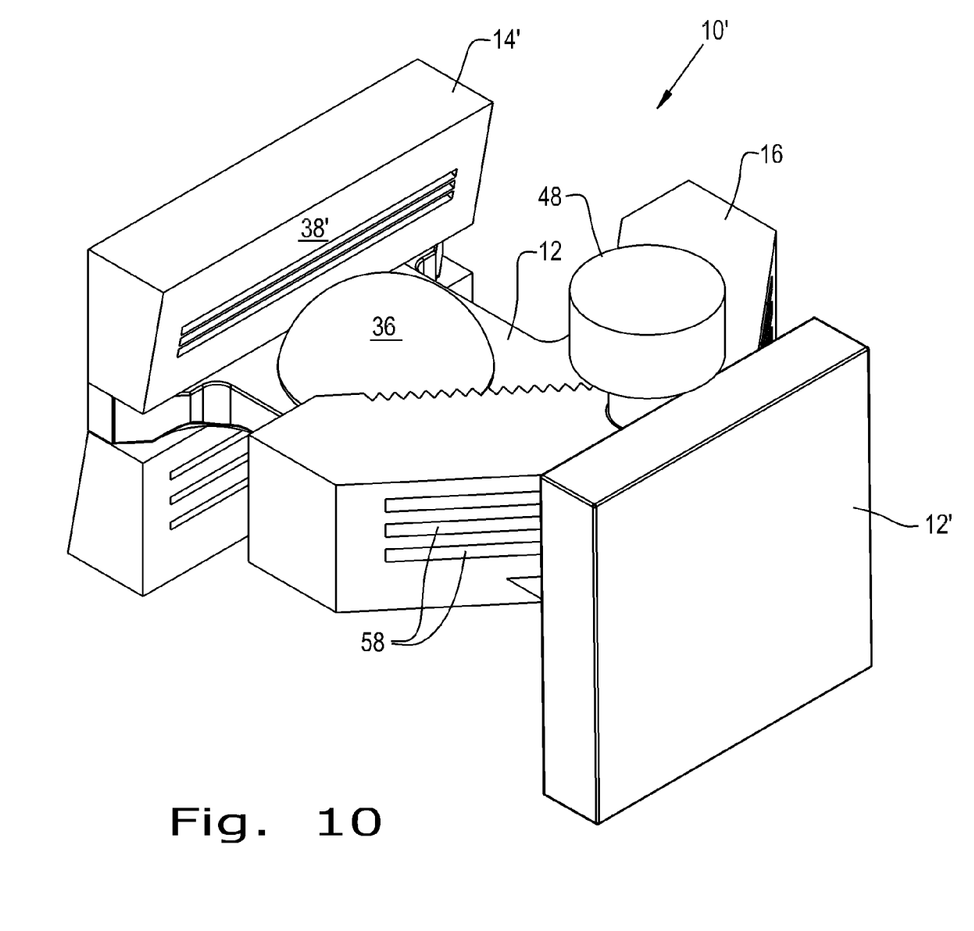
FIG. 10 is a perspective view of a second embodiment of the orthopaedic instrument of the present invention.
Figure 11:
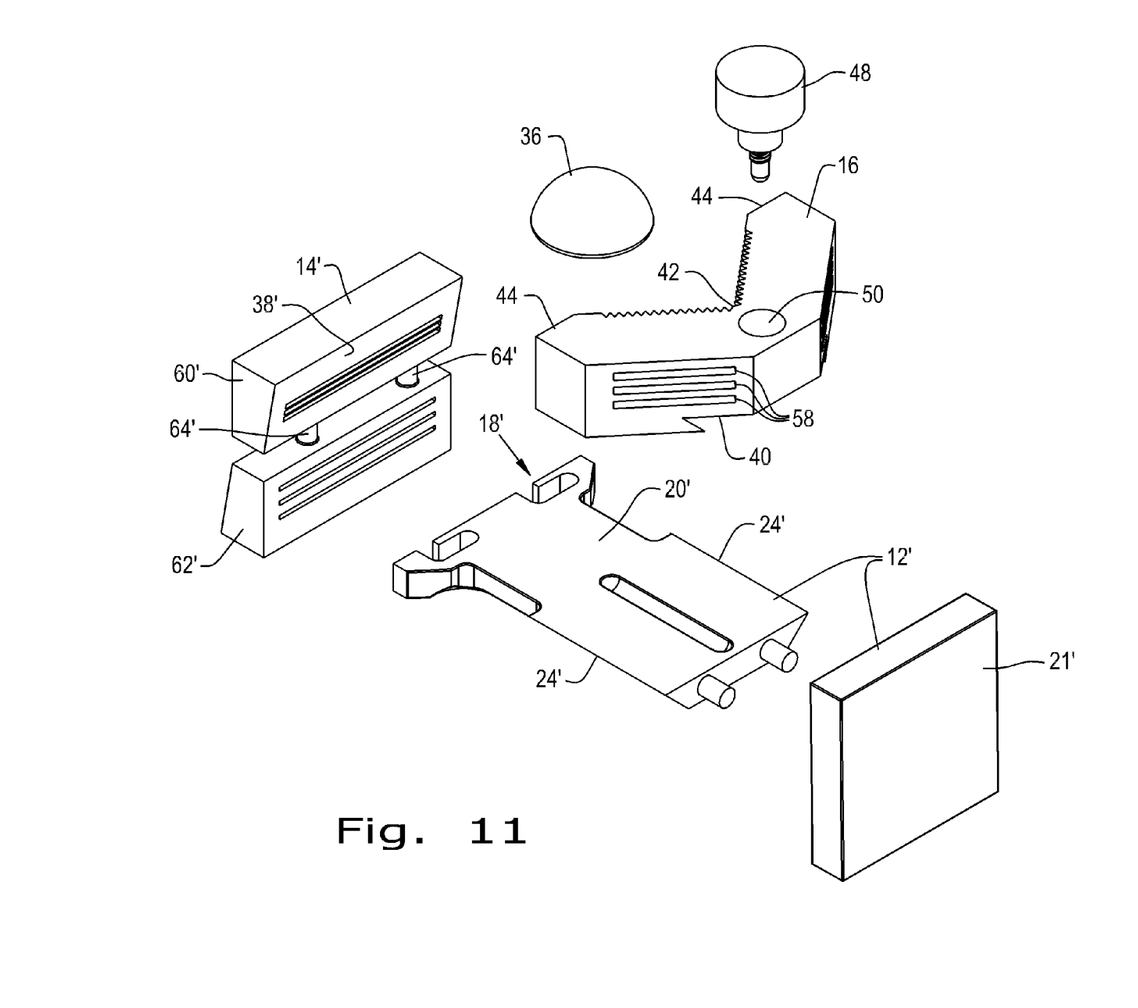
FIG. 11 is an exploded perspective view of the orthopaedic instrument of FIG. 10.

Referring now to FIGS. 10-11, there is shown a second embodiment of orthopaedic instrument 10' according to the present invention, including base plate 12', cutting block 14', and V-shaped vice member 16.

Figure 12:
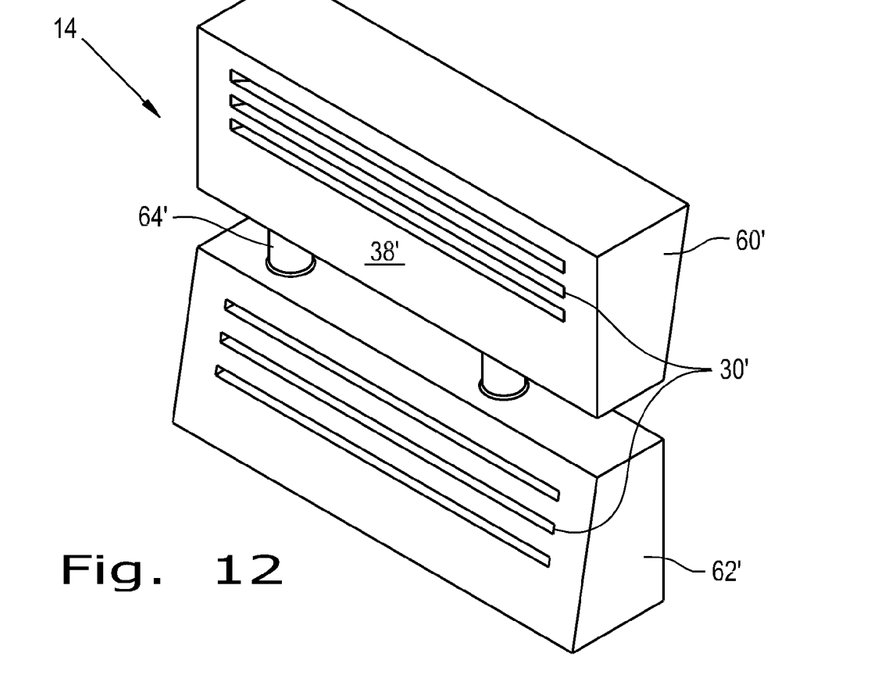
FIG. 12 is a perspective view of the cutting block shown in FIGS. 10 and 11.
Figure 13:
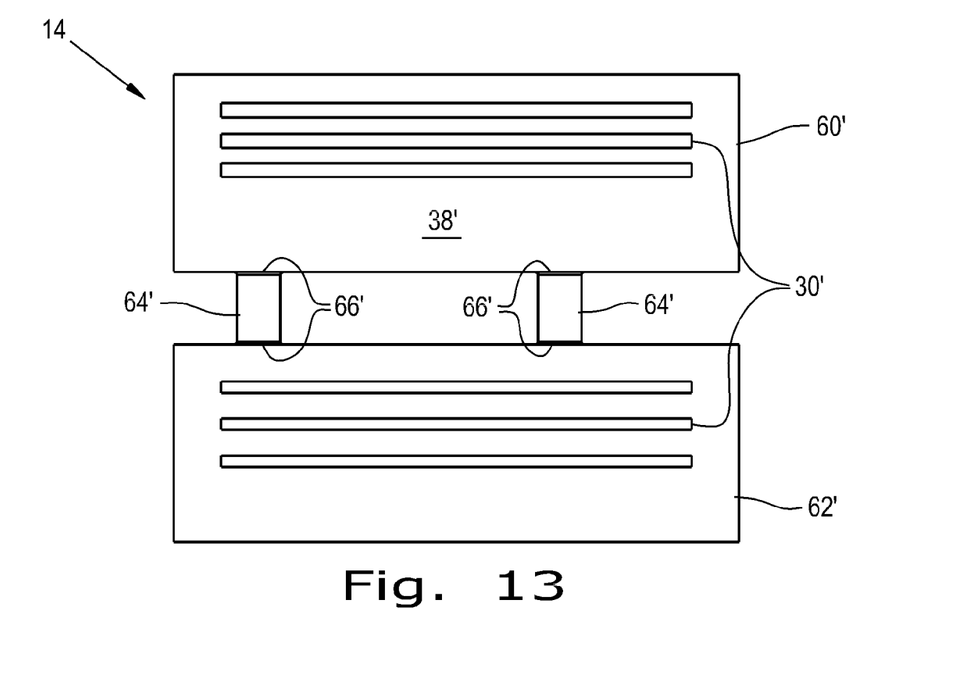
FIG. 13 is a side view of the cutting block of FIGS. 10-12.
Figure 14:
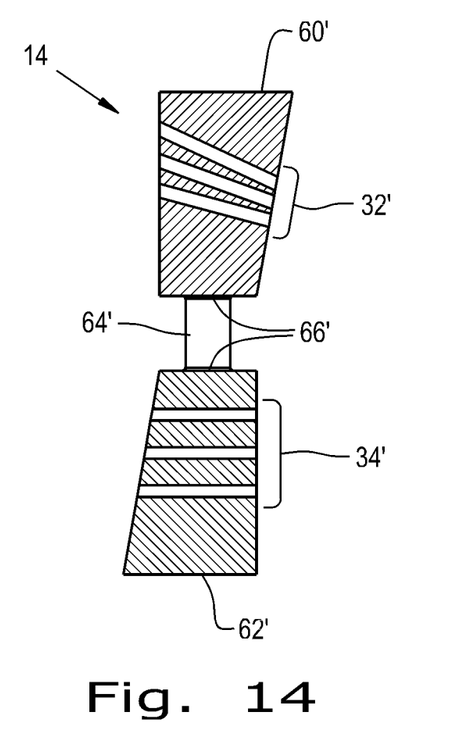
FIG. 14 is a sectional end view of the cutting block of FIGS. 10-13.

According to this embodiment of orthopaedic instrument 10', cutting block 14' includes a pair of opposing ends 60', 62' separated by at least one structural member 64', for example 2 structural members 64', as illustrated in FIGS. 12-14. Each opposing end 60', 62' is coupled with an end 66' of structural members 64'. Structural members 64' are sized and shaped to be received by end 18' of base plate 12'. Opposing ends 60', 62' each include a plurality of cutting slots 30' in a predetermined pattern and each of cutting slots 30' have a predetermined configuration, illustrated in FIGS.

12-14, which can be the same or different than the arrangement of cutting 30 slots of the first embodiment of the present invention, as set forth more fully above. Cutting block 14' further includes a face 38' which increasingly extends toward V-shaped vice member 16' as it extends away from elongate planer portion 20' of base plate 12', as illustrated in FIGS. 12 and 14. In this embodiment, cutting block 14' is also configured to be rotatable 180 degrees to switch between a first set 32' of cutting slots 30' to a second set 34' of cutting slots 30'.

Figure 15:
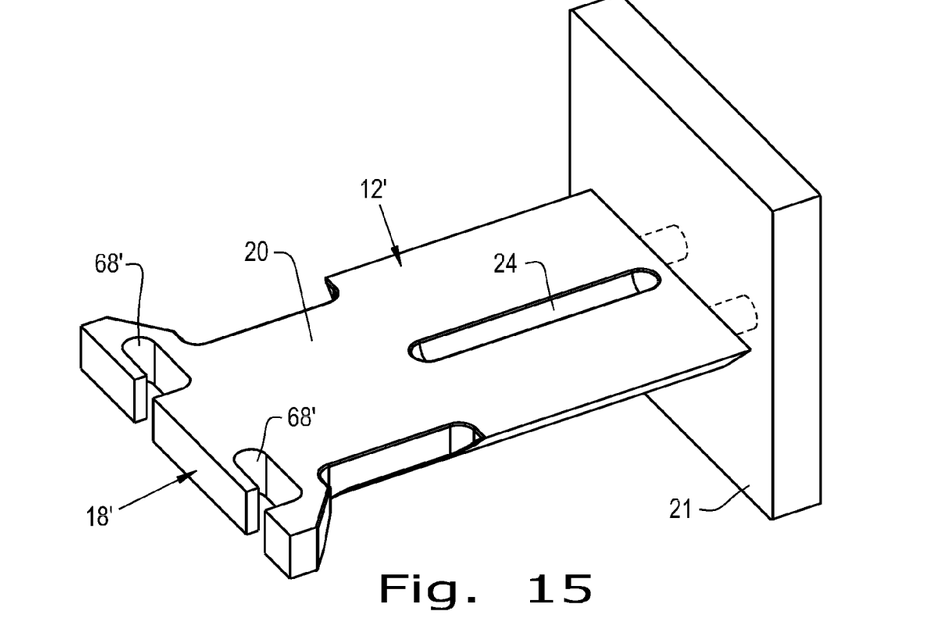
FIG. 15 is a perspective view of the base plate shown in FIGS. 10-11.
Figure 16:
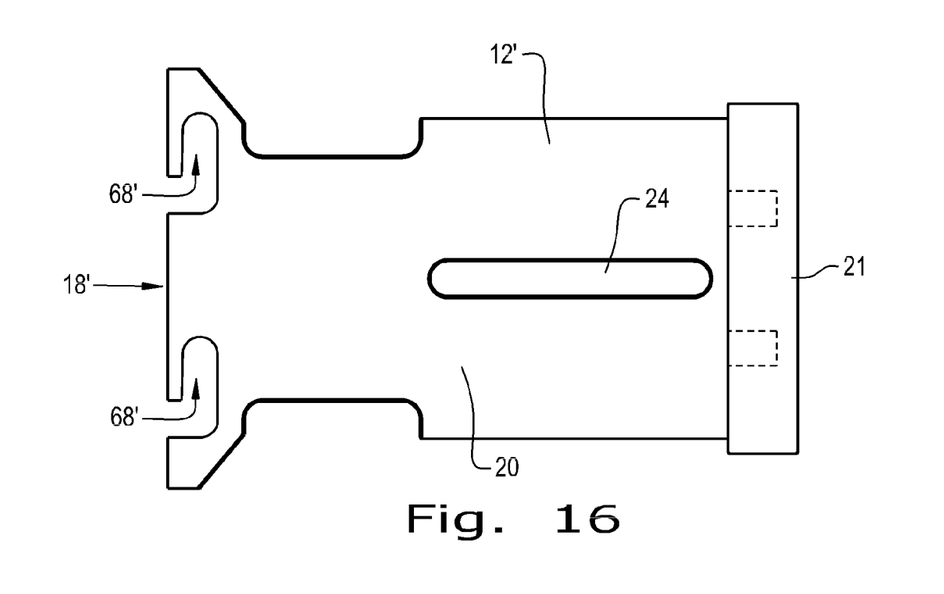
FIG. 16 is a top view of the base plate of FIGS. 10-11 and 15.
Figure 17:
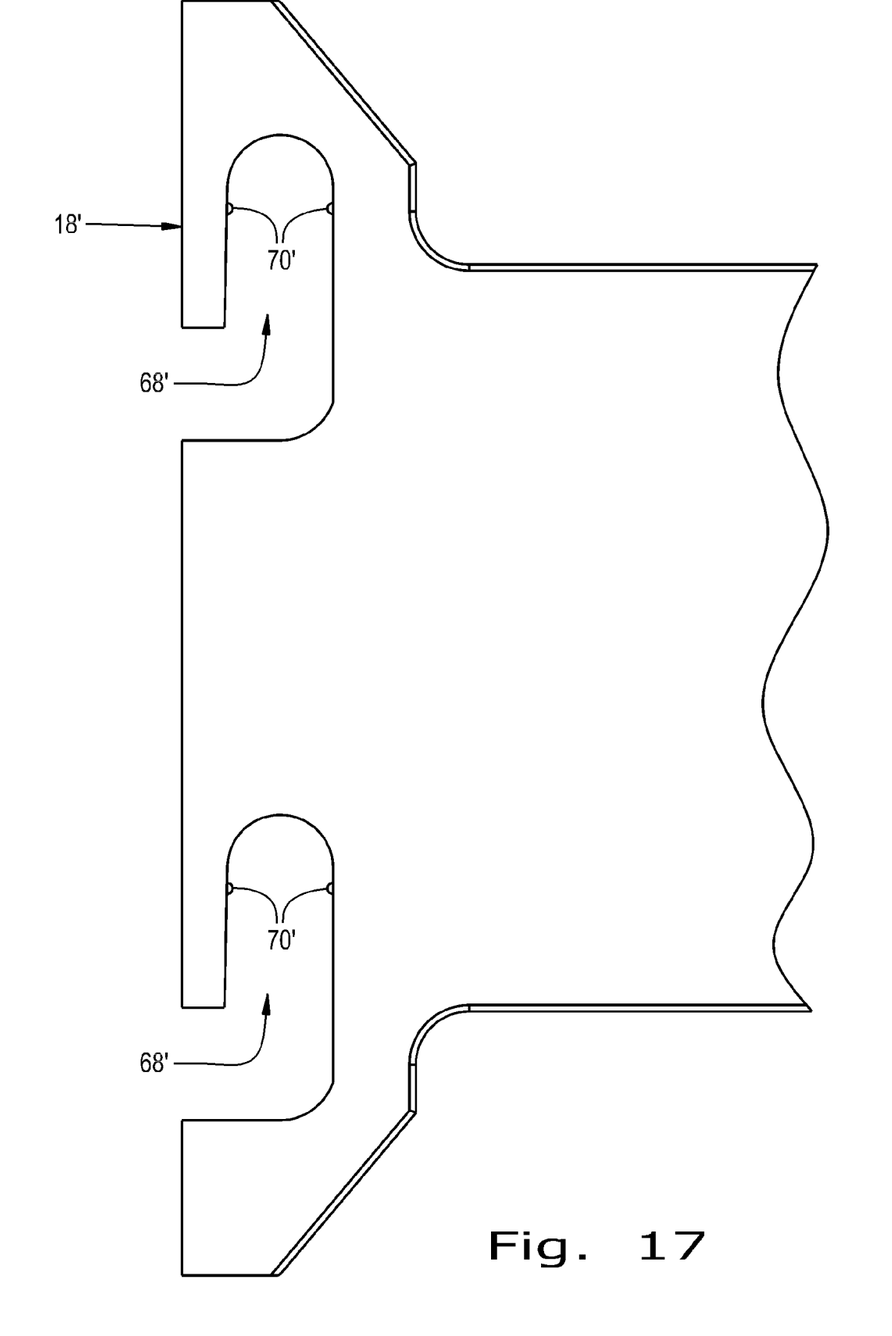
FIG. 17 is a top view of the finger slots in the base plate of FIGS. 15-16.

Referring now to FIGS. 15-17, end 18' of base plate 12' includes a pair of, for example, finger slots finger slots 68', which are sized and shaped to receive corresponding structural members 64' of cutting block 14'. Finger slots 68' can further include at least one, for example a pair of flexible members 70', shown in FIG. 17, which is compressed as structural members 64' (FIGS. 12-14) are slid past and then return to substantially their original configuration when structural members 64' are past flexible members 70', thereby securely coupling cutting block 14' and base plate 12' together. Although FIG. 17 illustrates one embodiment of the coupling of cutting block 14 and base plate 12' together, cutting block 14' and base plate 12' can be coupled together utilizing other conventional coupling mechanisms, for example welding, and the scope of the invention is not limited by the coupling mechanism illustrated in FIG. 17.

The present invention also provides a method of producing a custom bone. The method set forth includes removably locking cutting block 14 to end 18 of a base plate 12, as illustrated, for example, in FIGS. 1A and 1B. The step of removably locking cutting block 14 to the end 18 of the base plate 12 can further include using a fastener, for example a thumb screw, bolt or pin, to secure the cutting block 14 in position. A V-shaped vice member 16 is slidably coupled with the base plate 12 toward and away from the cutting block 14, as illustrated in FIG. 2. This can be accomplished, for example, by slidingly coupling a dovetail mortise 40 of the V-shaped vice member 16 with a dovetail-shaped tenon 24 of the base plate 12. A bone 36 is inserted between the V-shaped vice member 16 and the base plate 12, as shown in FIGS. 1-2. The V-shaped vice member 16 is slidingly adjusted to a position against the bone 36 and a force is applied with vice member 16 against the bone 36 and toward the cutting block 14. The V-shaped vice member 16 is locked into position against the bone 36, for example, with a set screw 48, to secure the bone 36 in position against the cutting block 14, as illustrated in FIG. 1. The user can then custom shape the bone using a saw blade (not shown) and the cutting block 14. Once the cuts have been made with the saw blade, the user can then further manually trim the bone 36 using, for example, scissors, a rongeur, or an osteotome, to more precisely match the patient anatomy. Additionally, at least one dimension for the bone 36 can be predefined for the custom shaping of the bone 36. Such predefined dimensions can include, for example, a thickness, a draft angle, a width and a length. Pre-operative planning software and/or a computed tomography (CT) scan may be used to plan the size and shape of a bone that is specific to a particular patient's needs. Accordingly, the orthopaedic instrument 10 according to the present invention can be used in the inventive method to shape the bone 36 according to pre-operatively or operatively determined parameters in the operative room.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic instrument for securing a bone, comprising:
   a base plate having an end;
   a cutting block removably coupled with said end of said base plate, said cutting block having a plurality of cutting slots, each of said cutting slots having a predefined configuration; and
   a V-shaped vice member slidingly coupled with said base plate and movable toward and away from said cutting block, said vice member configured for centering the bone and applying a force against the bone toward said cutting block.

2. The orthopaedic instrument according to claim 1, said cutting block being configured for applying another force against the bone toward said base plate.

3. The orthopaedic instrument according to claim 2, wherein said cutting block has a face that increasingly extends toward said V-shaped vice member as it extends away from a plane of said base plate.

4. The orthopaedic instrument according to claim 1, said plurality of predefined cutting slots including a first set of cutting slots that are non-coplanar with said base plate and a second set of cutting slots which are coplanar with said base plate, each of said second set of cutting slots being positioned at a predefined distance from said base plate.

5. The orthopaedic instrument according to claim 4, wherein said cutting block is configured to be rotatable 180 degrees to switch from said first set of cutting slots to said second set of cutting slots and vice versa.

6. The orthopaedic instrument according to claim 5, said cutting block having a pair of opposing ends separated by at least one structural member, each of said pair of opposing ends being coupled with an opposing end of said structural member.

7. The orthopaedic instrument according to claim 6, wherein said at least one structural member is sized and shaped to be received within at least one corresponding finger slot on said end of said base plate.

8. The orthopaedic instrument according to claim 2, said cutting block having a through opening configured to slidingly receive a corresponding protrusion extending from said end of said base plate.

9. The orthopaedic instrument according to claim 1, said V-shaped vice member further comprising a plurality of teeth extending from an interior surface of said V-shaped vice member, said interior surface being directed toward said cutting block.

10. The orthopaedic instrument according to claim 9, wherein said plurality of teeth are arranged in a plurality of layers.

11. The orthopaedic instrument according to claim 10, wherein said plurality of layers of said teeth includes at least a first layer and a second layer, said first layer being positioned above said second layer extending beyond an end of said second layer toward said cutting block.

12. The orthopaedic instrument according to claim 1, said V-shaped vice member having a dovetail shaped mortise sized and shaped to slidingly receive a corresponding tenon of said base plate.

13. The orthopaedic instrument according to claim 1, said V-shaped vice member being secured at a predetermined position with a fastener.

14. The orthopaedic instrument according to claim 1, wherein the assembled instrument is configured for use in a first orientation for a horizontal cutting plane and a second orientation for a vertical cutting plane.

15. An orthopaedic instrument for securing a bone, comprising:
 a base plate having an end;
 a cutting block removably coupled with said end of said base plate and including a plurality of cutting slots having a predefined orientation, said cutting block being configured for applying a force against the bone toward said base plate; and
 a V-shaped vice member slidingly coupled with said cutting block and movable toward and away from said cutting block with said base plate, said V-shaped vice member being configured for applying another force to the bone toward said base plate and for applying a third force to the bone toward said cutting block.

16. The orthopaedic instrument according to claim 15, said vice being secured at a predetermined position with a fastener.

17. The orthopaedic instrument according to claim 16, wherein the assembled orthopaedic instrument is configured for use in a first orientation for a horizontal cutting plane and a second orientation or a vertical cutting plane.

18. The orthopaedic instrument according to claim 15, wherein said cutting block has a face that increasingly extends toward said V-shaped vice member as it extends away from a plane of said base plate.

19. The orthopaedic instrument according to claim 18, wherein said plurality of predefined cutting slots includes a first set of cutting slots that are non-coplanar with said base plate and a second set of cutting slots which are coplanar with said base plate, each of said second set of cutting slots being positioned at a predefined distance from said base plate.

20. A method of producing a custom bone, the method comprising the steps of:
 removably locking a cutting block to an end of a base plate, said cutting block having a plurality of cutting slots, each of said cutting slots having a predefined configuration;
 slidably coupling a V-shaped vice member with said base plate such that said V-shaped vice member is movable toward and away from said cutting block;
 inserting the bone between said V-shaped vice member and said base plate;
 slidingly adjusting said V-shaped vice member to a position against the bone;
 applying a first force with said V-shaped vice member against the bone toward said cutting block;
 locking said V-shaped vice member into said position against said bone to secure the bone in position against said cutting block; and
 custom shaping the bone.

\* \* \* \* \*

UNITED STATES PATENT AND TRADEMARK OFFICE
CERTIFICATE OF CORRECTION

PATENT NO. : 9,700,438 B2  
APPLICATION NO. : 14/297559  
DATED : July 11, 2017  
INVENTOR(S) : Kehres et al.

Page 1 of 1

It is certified that error appears in the above-identified patent and that said Letters Patent is hereby corrected as shown below:

On the Title Page

In item (57), in "Abstract", in Column 2, Line 1, delete "orthopedic" and insert --orthopaedic-- therefor Signed and Sealed this  
Nineteenth Day of March, 2019

Andrei Iancu  
*Director of the United States Patent and Trademark Office*